United States Patent
Stahmann et al.

(10) Patent No.: US 6,907,289 B2
(45) Date of Patent: Jun. 14, 2005

(54) TRIGGERED STORAGE OF DIAGNOSTIC DATA ASSOCIATED WITH COMPROMISED RESYNCHRONIZATION THERAPY

(75) Inventors: Jeffrey E. Stahmann, Ramsey, MN (US); Andrew P. Kramer, Stillwater, MN (US); David Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 490 days.

(21) Appl. No.: 09/991,522

(22) Filed: Nov. 20, 2001

(65) Prior Publication Data

US 2003/0097155 A1 May 22, 2003

(51) Int. Cl.[7] .............................................. A61N 1/362
(52) U.S. Cl. ............................................ 607/27; 607/9
(58) Field of Search ............................. 600/510; 607/4, 607/5, 9, 27, 28

(56) References Cited

U.S. PATENT DOCUMENTS

| | | | |
|---|---|---|---|
| 4,721,114 A | 1/1988 | DuFault et al. | 128/696 |
| 4,872,459 A | 10/1989 | Pless et al. | 128/419 PG |
| 4,880,005 A | 11/1989 | Pless et al. | 128/419 PG |
| 5,447,519 A * | 9/1995 | Peterson | 607/5 |
| 5,518,001 A | 5/1996 | Snell | 128/697 |
| 5,749,900 A | 5/1998 | Schroeppel et al. | 607/4 |
| 5,749,907 A | 5/1998 | Mann | 607/27 |
| 5,792,205 A | 8/1998 | Alt et al. | 607/32 |
| 5,825,283 A | 10/1998 | Camhi | 340/438 |
| 5,861,013 A | 1/1999 | Peck et al. | 607/28 |
| 5,867,386 A | 2/1999 | Hoffberg et al. | 364/188 |
| 5,875,108 A | 2/1999 | Hoffberg et al. | 364/146 |
| 5,901,246 A | 5/1999 | Hoffberg et al. | 382/209 |
| 5,903,454 A | 5/1999 | Hoffberg et al. | 364/188 |
| 5,920,477 A | 7/1999 | Hoffberg et al. | 364/148 |
| 5,935,081 A | 8/1999 | Kadhiresan | 600/513 |
| 5,974,340 A | 10/1999 | Kadhiresan | 607/18 |
| 5,987,352 A | 11/1999 | Klein et al. | 600/509 |
| 6,035,233 A | 3/2000 | Schroeppel et al. | 600/515 |
| 6,044,299 A | 3/2000 | Nilsson | 607/19 |
| 6,058,329 A | 5/2000 | Salo et al. | 607/17 |
| 6,080,187 A | 6/2000 | Alt | 607/32 |
| 6,144,878 A | 11/2000 | Schroeppel et al. | 600/515 |
| 6,272,377 B1 | 8/2001 | Sweeney et al. | 600/515 |
| 6,409,675 B1 | 6/2002 | Turcott | 600/508 |
| 6,438,421 B1 | 8/2002 | Stahmann et al. | 607/9 |
| 6,453,201 B1 | 9/2002 | Daum et al. | 607/62 |
| 6,470,210 B1 | 10/2002 | Chen et al. | 600/515 |
| 6,480,742 B2 | 11/2002 | Stahmann et al. | 607/27 |
| 6,571,121 B2 | 5/2003 | Schroeppel et al. | 600/515 |
| 6,571,122 B2 | 5/2003 | Schroeppel et al. | 600/515 |
| 6,668,194 B2 * | 12/2003 | VanHout | 607/9 |

(Continued)

OTHER PUBLICATIONS

Daum, Douglas R., "Implantable Medical Device With Voice Responding and Recording Capacity", U.S. Appl. No. 09/421,746, filed Oct. 20, 1999 (now abandoned), 13 pgs.

Dyjach, John A., et al., "Method for Exclusion of Ectopic Events From Heart Rate Variability Metrics", U.S. Appl. No. 10/728,124, filed Dec. 4, 2003, 21 pgs.

Dyjach, John A., "Trended Measurement of Cardiac Resynchronization Therapy", U.S. Appl. No. 10/730,760, filed Dec. 8, 2003, 54 pgs.

Primary Examiner—Kennedy Schaetzle
Assistant Examiner—Kristen Mullen
(74) Attorney, Agent, or Firm—Schwegman, Lundberg, Woessner & Kluth, P.A.

(57) ABSTRACT

A method for operating a cardiac rhythm management device used for cardiac resynchronization therapy in which the storage of diagnostic data is triggered by detection of a condition indicating that the effectiveness of the therapy has been compromised. Such diagnostic data may be electrograms or marker/interval data acquired from the sensing channels of the device.

34 Claims, 2 Drawing Sheets

U.S. PATENT DOCUMENTS

| | | |
|---|---|---|
| 6,678,547 B2 | 1/2004 | Carlson et al. ............. 600/515 |
| 2002/0016550 A1 | 2/2002 | Sweeney et al. ............ 600/515 |
| 2002/0082509 A1 * | 6/2002 | Vanderlinde et al. ....... 600/510 |
| 2002/0120306 A1 | 8/2002 | Zhu et al. ..................... 607/25 |
| 2002/0193847 A1 | 12/2002 | Daum et al. .................. 607/60 |
| 2003/0060851 A1 * | 3/2003 | Kramer et al. ................. 607/9 |

* cited by examiner

TRIGGERED STORAGE OF DIAGNOSTIC DATA ASSOCIATED WITH COMPROMISED RESYNCHRONIZATION THERAPY

FIELD OF THE INVENTION

This invention pertains to methods and apparatus for cardiac rhythm management. In particular, the invention relates to methods and apparatus for providing cardiac resynchronization therapy.

BACKGROUND

Cardiac rhythm management devices are implantable devices that provide electrical stimulation to selected chambers of the heart in order to treat disorders of cardiac rhythm. An implantable pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Heart failure refers to a clinical syndrome in which an abnormality of cardiac function causes a below normal cardiac output that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site is spread throughout the myocardium only via the much slower conducting muscle fibers of either the atria or the ventricles, and not the specialized conduction pathways. Most pacemaker patients can still maintain more than adequate cardiac output with artificial pacing, but the diminishment in cardiac output may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

SUMMARY OF THE INVENTION

Cardiac rhythm management devices for delivering resynchronization therapy may be programmed with a number of different parameter settings that affect the manner in which resynchronization paces are delivered. These parameters can be initially programmed after implantation while a physician is monitoring the patient so that the resynchronization therapy is delivered optimally. The patient's condition may change subsequently, however, and result in a loss or degradation of resynchronization therapy if the parameters are unaltered. Also, the operating characteristics of the device may change after implantation, either due to changes in the device itself or environmental influences, and that may also interfere with the optimal delivery of resynchronization therapy. Both of these situations may arise transiently and not be present when the patient is being evaluated during clinical follow-up. It would be useful for a physician to have data that is recorded at the time such compromise of resynchronization occurred in order to assist in the diagnosis and correction of the problem causing such compromise. In accordance with the invention, an implantable cardiac rhythm management device is configured to store certain data acquired by its sensing channels when a triggering condition is detected that indicates that some degradation of the resynchronization therapy has occurred. The triggering conditions that initiate such data storage may relate, for example, to situations in which there is a reduced frequency of pacing in one or more of the device's pacing channels. The stored data may take the form of electrograms recorded from one or more sensing channels or data derived therefrom such as intervals between detected events.

DETAILED DESCRIPTION

The present invention relates to a method for triggering the storage of data by a cardiac rhythm management device configured to deliver cardiac resynchronization therapy. What follows is a description of the method as well as of the hardware components and operating modes of a device in which the method may be implemented.

1. Hardware Platform

In the embodiment to be described, the invention is implemented with a control unit made up of a microprocessor executing programmed instructions in memory. It should be appreciated, however, that certain functions of a cardiac rhythm management device could be controlled by custom logic circuitry either in addition to or instead of a programmed microprocessor. The term "controller" as used herein should therefore be taken to encompass either custom circuitry (i.e., dedicated hardware) or a microprocessor executing programmed instructions contained in a processor-readable storage medium along with associated circuit elements.

Pacemakers and other types of implantable cardiac rhythm management devices are typically implanted subcutaneously or submuscularly in a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker and exceeds a specified threshold is referred to as an atrial sense or ventricular sense, respectively. In order to cause such a contraction in the absence of an intrinsic beat, a pacing pulse (either an atrial pace or a ventricular pace) with energy above a certain pacing threshold is delivered to a heart chamber.

Figure 1:
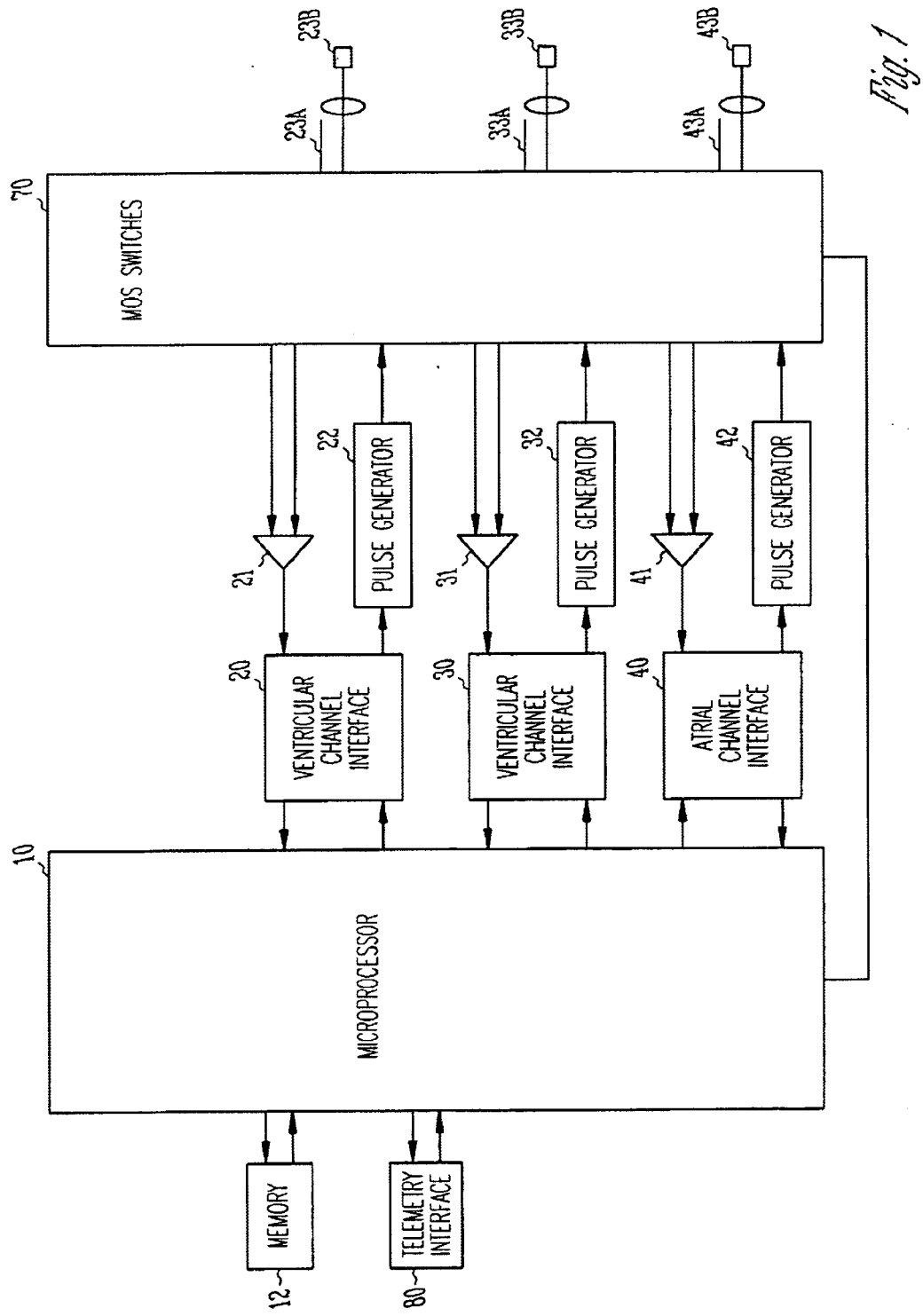
FIG. 1 is a system diagram of a pacemaker configurable for delivering resynchronization therapy.

A block diagram of a multi-site pacemaker having three sensing/pacing channels is shown in FIG. 1. (As the term is used herein, a "pacemaker" should be taken to mean any cardiac rhythm management device, such as an implantable cardioverter/defibrillator, with a pacing functionality.) The control unit of the pacemaker is made up of a microprocessor 10 communicating with a memory 12 via a bidirectional data bus, where the memory 12 typically comprises a ROM (read-only memory) for program storage and a RAM (random-access memory) for data storage. The control unit could be implemented by other types of logic circuitry (e.g., discrete components or programmable logic arrays) using a state machine type of design, but a microprocessor-based system is preferable. The control unit is capable of operating the pacemaker in a number of programmed modes where a programmed mode defines how pacing pulses are output in response to sensed events and expiration of time intervals. A telemetry interface 80 is also provided for communicating with an external programmer.

The multiple sensing/pacing channels may be configured to deliver biventricular pacing, biatrial pacing, or multi-site pacing of a single chamber. Illustrated in FIG. 1 is a configuration with one atrial and two ventricular sensing/pacing channels for delivering biventricular pacing. The atrial sensing/pacing channel in FIG. 1 comprises ring electrode 43a, tip electrode 43b, sense amplifier 41, pulse generator 42, and an atrial channel interface 40 which communicates bidirectionally with a port of microprocessor 10. The device also has two ventricular sensing/pacing channels that similarly include ring electrodes 23a and 33a, tip electrodes 23b and 33b, sense amplifiers 21 and 31, pulse generators 22 and 32, and ventricular channel interfaces 20 and 30. Incorporated into each sensing/pacing channel is thus a pacing channel made up of the pulse generator connected to the electrode and a sensing channel made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. For each channel, the same electrode pair is used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory. The controller 10 interprets sense signals from the sensing channels and controls the delivery of paces in accordance with a pacing mode. The sensing circuitry of the pacemaker generates atrial and ventricular senses when voltages sensed by the electrodes of a particular channel exceed a specified threshold. Pacing algorithms employ such senses to trigger or inhibit pacing. The sense signals from each channel can also be recorded in memory for a specified period of time to constitute an electrogram that can later be transmitted via the telemetry link to an external programmer. An electrogram is analogous to a surface ECG and provides a temporal record of cardiac depolarization and repolarization that occurs during either intrinsic or paced beats. The recording of an electrogram may be triggered by the detection of certain events or conditions such as the onset of a tachyarrhythmia in order to provide diagnostic information to a clinician. As described below, electrograms can also provide useful information in evaluating the functioning of the device in providing cardiac resynchronization therapy.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker operating in a ventricular pacing mode, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized contractions of the atria and/or ventricles and thereby improves pumping efficiency. Although resynchronization pacing may be delivered to only one heart chamber or multiple sites of a single chamber, it most often involves pacing both ventricles in accordance with a biventricular resynchronization pacing mode as described below. Ventricular resynchronization pacing is useful in treating heart failure because, although not directly ionotropic, resynchronization results in a more coordinated contraction of the ventricles with improved pumping efficiency and increased cardiac output.

One way to deliver resynchronization therapy is to pace a site with a synchronous bradycardia pacing mode and then deliver one or more resynchronization paces to one or more additional pacing sites in a defined time relation to one or more selected sensing or pacing events that either reset escape intervals or trigger paces in the bradycardia pacing mode. The site paced with the bradycardia mode may be referred to as a rate site or rate chamber, while the site paced with resynchronization paces may be referred to as a synchronized site or synchronized chamber. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace (i.e., the right ventricle is a rate chamber and the left ventricle is a synchronized ventricle).

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP thus provides a means to inhibit pacing of the synchronized chamber when a pace might be delivered during the vulnerable period or when it might compromise pumping efficiency by pacing the chamber too close to an intrinsic beat.

4. Triggered Storage of Diagnostic Data

In the description that follows, a device such as that depicted in FIG. 1 is assumed to be configured to deliver ventricular resynchronization therapy (VRT) in a biventricular pacing mode with the right ventricle serving as the rate chamber. Other embodiments may employ the left ventricle as the rate chamber. When such a device is operating in a patient, resynchronization therapy is degraded during cardiac cycles in which one or both ventricles fail to receive a pace. It is therefore desirable for pacing to be frequent, and parameter settings or conditions that allow more natural beats to occur reduce the effectiveness of the therapy.

A number of factors can result in a loss of or reduction of pacing to either or both ventricles in a biventricular resynchronization pacing mode. For example, in a VVI or VVIR mode, ventricular paces will be inhibited by intrinsic activity, and less frequent pacing will result if the LRL is set too low or, in the case of rate-adaptive pacing, if the exertion level sensor does not adequately increase the LRL. In an atrial tracking mode, if the patient's intrinsic PR interval is too short as compared with the programmed atrioventricular escape interval, intrinsic ventricular beats will occur more frequently. Maximum limits on the pacing rate (e.g., limits on the sensor-indicated rate or the atrial tracking rate) that are too low can also result in more frequent intrinsic beats than are desirable, as can incorrect parameter settings of pacing modes in which the escape intervals are dynamically adjusted in order to suppress intrinsic beats (i.e., ventricular rate regularization or other types of overdrive pacing).

Underpacing may also be the result of oversensing in a sensing channel that either restarts escape intervals or triggers protective periods. Excessive noise or inadequate refractory periods in the rate channel would result in underpacing of both ventricles, while such noise or under-refractoriness in the synchronized channel would cause underpacing of only the synchronized chamber. For example, in RV-based biventricular pacing, noise in the LV channel or an LVPP (left ventricular protection period) that is too long would cause underpacing of only the left ventricle. Underpacing of only the synchronized chamber can also occur if the offset interval becomes too short due to, for example, changes in the intrinsic RV-LV conduction interval. Other factors, such as insufficient pacing energy which can come about due to equipment failure or changes in the myocardial substrate, may reduce the effectiveness of pacing without necessarily affecting the pacing frequency.

When a patient undergoing resynchronization therapy is evaluated during follow-up, clinical symptoms or other indicia may indicate that the therapy has become less effective and that some adjustments should be made. It may be difficult to ascertain, however, exactly what parameters should be changed in order to re-optimize the therapy. Although the operation of the implanted device may be monitored with an external programmer, some of the problems listed above may only occur intermittently or under special circumstances. It would therefore be useful for the physician to have diagnostic data that is recorded by the device during the time at which an instance of compromised resynchronization therapy occurred. The present invention provides a method for operating a cardiac rhythm management device in which recording of particular data acquired through its sensing channels is triggered by detection of a condition that indicates some degradation in resynchronization therapy. Such a triggering condition may be based upon a presently detected parameter or a parameter derived from data collected over a specified time period. For example, the device may maintain running totals of the number of paced and unpaced cycles so that data storage is triggered when underpacing is detected such as: 1) if the percent of paced cycles over a certain period of time in either or both ventricles drops below a specified threshold or drops below a specified threshold within a particular rate range, or 2) if the number of consecutive intrinsic beats exceeds a specified threshold. The device may also keep track of other parameters that may be used to trigger recording of data such as if the number of times a pace has been inhibited by the synchronized-chamber protective period within a specified time interval exceeds a specified limit value, or if the number of triggered paces over specified time interval exceeds a specified limit value. The device may also periodically measure the intrinsic PR interval by detecting the time interval between atrial and ventricular senses during unpaced beats so that data storage is triggered when the measured PR interval has deviated a defined percentage from the intrinsic PR interval measured during the last optimization. Another possible triggering condition is whenever the prescribed (i.e. programmed) cardiac synchronization therapy is consistently not delivered. For example the programmed pacing site(s), AV delay, and synchronization chamber offset can be defined as the pertinent programmed cardiac synchronization therapy parameters. Then, whenever it is detected that therapy is not delivered according to these parameters and at a predetermined consistency, data storage is triggered.

Since the device may have multiple triggering conditions, another beneficial capability would be to indicate which triggering condition caused a particular storage event. Additional statistical information regarding the condition may therefore be stored, such as the actual percentage of paced ventricular beats or average PR interval for a specified time interval preceding the event. Also, additional data regarding the condition of the patient may be useful in diagnosing the problem associated with the data storage. Therefore the device may also store items such as atrial rate, ventricular rate, activity level, respiration rate, autonomic balance, date, or time. In addition to the data stored when a triggering condition is met, the system could also continuously store information regarding the triggering parameters. In one embodiment, for example, the device could continuously store the percentage of time resynchronization therapy is being delivered. This data could then be displayed as a percentage trend over time.

In many instances, it is likely that the conditions that trigger storage of data could occur many times in a relatively short period of time due to essentially the same problem. In such cases, storage of what would amount to multiple data records that relate to that problem would waste memory and provide little diagnostic value over a single storage event. To more effectively utilize the limited memory in the implanted device and to minimize data presentation to the user, the device may limit the number of storage events that are due to a particular triggering condition within a specified period of time.

It may be important to inhibit triggering of data storage while certain pathological conditions exist. For example, during an episode of ventricular tachycardia or ventricular fibrillation, delivery of cardiac resynchronization therapy is normally inhibited. Therefore, although the conditions for triggering data storage may be otherwise met, storing data for the purposes of diagnosing lack of cardiac resynchronization therapy would be inappropriate in this situation. Other examples of conditions where data storage may be withheld or the conditions for triggering data storage may be modified include atrial arrhythmias, device malfunction and temporary programming used for diagnostic purposes.

When a triggering condition is detected, the device begins recording data from the atrial and/or ventricular sensing channels for a specified storage time. In one embodiment, the recorded data are electrograms represented by the digitized and stored voltage values received by the sensing channels. Since it is often useful for the physician to understand the situation immediately prior to the time when the triggering condition is detected, electrograms reflecting data collected just prior to detection of the triggering condition could be stored as well as those reflecting subsequently collected data. This may be implemented by the device continuously storing data in a first-in-first-out queue. The data in the queue can then be stored in a more permanent storage location along with subsequently collected data when a triggering condition is detected.

Figure 2:
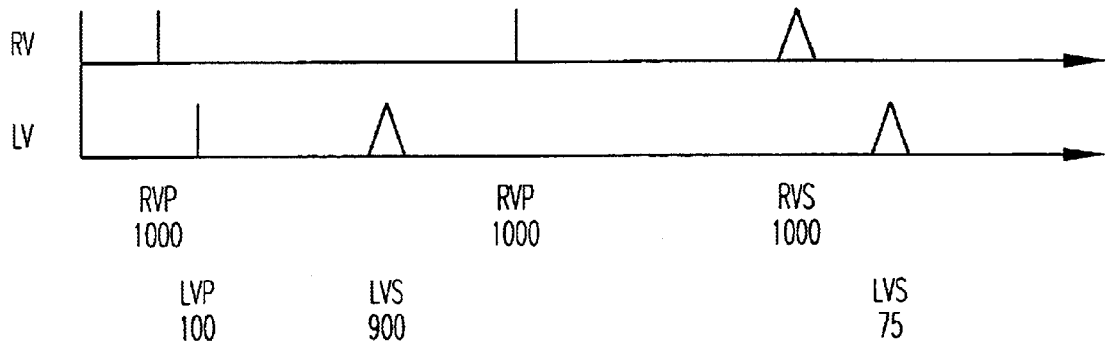
FIG. 2 is an exemplary display of marker/interval data.

Storing electrograms requires a considerable amount of memory, typically 150–200 bytes per cycle. As an alternative, therefore, markers representing sensed and paced events along with time intervals between the events may be stored instead. Another alternative for reducing the amount of memory required is to retain less information on older events. In one embodiment electrograms, markers and intervals would be stored for the most recent events where detailed information is most useful and only markers and intervals would be stored for older events where less information may be required. FIG. 2 shows an example of such markers and intervals as they might be displayed by an external programmer. Timelines are displayed representing electogram data for the right and left ventricular sensing/pacing channels, labeled RV and LV, respectively. Underneath the timelines are two lines of markers output by the display for both ventricular channels. Each marker in the top line represents right ventricular events, and each marker in the bottom line represents left ventricular events. Associated with each marker is an intraventricular interval which indicates the time interval between the event represented by the marker and another ventricular event. In this example, the interval displayed with each right and left ventricular marker is the interval from the previous right ventricular event. Storing markers and intervals requires considerably less memory, on the order of 8–10 bytes per cycle.

Figure 3:
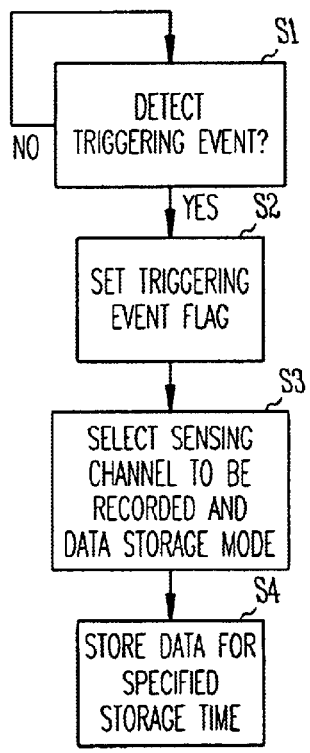
FIG. 3 is a flowchart illustrating an exemplary implementation of the triggered data storage method.

Many VRT problems can be diagnosed with only markers and intervals. Electrograms, however, may be beneficial in some cases and essential in others. Also, many VRT problems can be diagnosed with electrograms from only two channels, but the particular two channels that are required depends upon the specific problem. For example, loss of pacing in both ventricular channels due to the intrinsic PR interval being shorter than the programmed atrio-ventricular interval can be diagnosed with data from the atrial and right ventricular channels. Loss of left ventricular pacing due to far-field sensing of right ventricular depolarizations in the left ventricular channel, on the other hand, is best diagnosed with data from the left and right ventricular channels. If memory constraints prevent recording data from all three sensing channels, the particular channels from which diagnostic data is to be stored may be selected in accordance with the particular triggering event that is detected. Whether an electrogram or marker/interval data is stored may also be made to depend upon the particular triggering event. FIG. 3 is a flow chart illustrating an exemplary embodiment of the method as it could be implemented by programming of the controller. A triggering event is looked for at step S1, and, if one is detected, a flag indicating the event is set at step S2. The sensing channels from which diagnostic data is to be recorded and the storage mode to be used, either electrograms or marker/interval data, are then selected at step S3 in accordance with the particular triggering event detected at step S1. Diagnostic data is then recorded for a defined storage time at step S4.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

sensing cardiac electrical activity via a plurality of sensing channels;

outputting pacing pulses through plurality of pacing channels in order to pace both ventricles in accordance with a cardiac resynchronization pacing mode; and, storing data received from one or more selected sensing channels in a memory upon detection of a triggering condition indicating a decrease in pacing frequency over a specified period of time.

2. The method of claim 1 wherein the stored data is an electrogram from the selected sensing channel.

3. The method of claim 1 wherein the stored data is marker/interval data reflecting sensing and pacing events in the selected sensing channel and time intervals therebetween.

4. The method of claim 1 wherein the triggering condition is when the percent of paced cycles over a specified period of time in either or both ventricles has dropped below a specified threshold value.

5. The method of claim 1 wherein the triggering condition is when the percent of paced cycles over a specified period of time in either or both ventricles has dropped below a specified threshold value within a particular rate range.

6. The method of claim 1 wherein the triggering condition is when the number of consecutive intrinsic beats has exceeded a specified threshold value.

7. The method of claim 1 wherein the triggering condition is when the number of times a pace has been inhibited by a synchronized-chamber protective period within a specified time interval has exceeded a specified limit value.

8. The method of claim 1 wherein the triggering condition is when the number of triggered paces in a specified time interval has exceeded a specified limit value.

9. The method of claim 1 further comprising periodically measuring the intrinsic PR interval by detecting the time interval between atrial and ventricular senses during unpaced beats, and wherein an additional triggering condition is when the measured PR interval has deviated a defined percentage from a previously measured intrinsic PR interval.

10. The method of claim 1 wherein the particular sensing channel from which data is to be stored and whether the data is to be stored as an electrogram or marker/interval data depends upon detection of a particular triggering condition.

11. The method of claim 1 further comprising, upon detection of a triggering condition, storing in memory data received from one or more selected sensing channels during a specified time immediately preceding detection of the triggering condition.

12. The method of claim 1 wherein an additional triggering condition is when the delivered therapy is inconsistent with the programmed cardiac resynchronization therapy.

13. The method of claim 1 further comprising storing the triggering condition in a memory upon its detection.

14. The method of claim 1 further comprising storing statistical data regarding a triggering parameter in a memory upon detection of a triggering condition.

15. The method of claim 1 further comprising storing additional data regarding the physical condition of a patient in whom the device is implanted in a memory upon detection of a triggering condition.

16. The method of claim 1 wherein the data is stored for a specified storage time upon detection of a triggering condition.

17. The method of claim 1 further comprising inhibiting storage of data upon detection of a triggering condition if a pathological condition is also detected.

18. A cardiac rhythm management device, comprising:
a plurality of sensing channels, each such channel comprising an electrode connected to a sense amplifier for sensing cardiac electrical activity;
a plurality of pacing channels, each such channel comprising an electrode connected to a pulse generator for delivering pacing pulses to a heart chamber;
a controller for controlling the delivery of pacing pulses and for receiving data from the sensing channels;
wherein the controller is programmed to:
pace both ventricles in accordance with a ventricular resynchronization pacing mode; and,
store data received from one or more selected sensing channels in a memory upon detection of a triggering condition indicating a decrease in pacing frequency over a specified period of time.

19. The device of claim 18 wherein the stored data is an electrogram from the selected sensing channel.

20. The device of claim 18 wherein the stored data is marker/interval data reflecting sensing and pacing events in the selected sensing channel and time intervals therebetween.

21. The device of claim 18 wherein the triggering condition is when the percent of paced cycles over a specified period of time in either or both ventricles has dropped below a specified threshold value.

22. The device of claim 18 wherein the triggering condition is when the percent of paced cycles over a specified period of time in either or both ventricles has dropped below a specified threshold value within a particular rate range.

23. The device of claim 18 wherein the triggering condition is when the number of consecutive intrinsic beats has exceeded a specified threshold value.

24. The device of claim 18 wherein the triggering condition is when the number of times a pace has been inhibited by a synchronized-chamber protective period within a specified time interval has exceeded a specified limit value.

25. The device of claim 18 wherein the triggering condition is when the number of triggered paces in a specified time interval has exceeded a specified limit value.

26. The device of claim 18 wherein the controller is programmed to periodically measure the intrinsic PR interval by detecting the time interval between atrial and ventricular senses during unpaced beats, and wherein an additional triggering condition is when the measured PR interval has deviated a defined percentage from a previously measured intrinsic PR interval.

27. The device of claim 18 wherein the particular sensing channel from which data is to be stored and whether the data is to be stored as an electrogram or marker/interval data depends upon detection of a particular triggering condition.

28. The device of claim 18 wherein data received from one or more selected sensing channels during a specified time immediately preceding detection of a triggering condition is stored in a memory upon detection of the triggering condition.

29. The device of claim 18 wherein an additional triggering condition is when the delivered therapy is inconsistent with the programmed cardiac resynchronization therapy.

30. The device of claim 18 wherein the triggering condition is stored in a memory upon its detection.

31. The device of claim 18 wherein statistical data regarding a triggering parameter is stored in a memory upon detection of a triggering condition.

32. The device of claim 18 wherein additional data regarding the physical condition of a patient in whom the device is implanted is stored in a memory upon detection of a triggering condition.

33. The device of claim 18 wherein the data is stored for a specified storage time upon detection of a triggering condition.

34. The device of claim 18 wherein storage of data upon detection of a triggering condition is inhibited if a pathological condition is also detected.

* * * * *